United States Patent

Gee

[11] Patent Number: 6,100,223
[45] Date of Patent: Aug. 8, 2000

[54] METHOD OF CONVERTING OLEFINS INTO MIXTURES OF SECONDARY ESTERS, PRODUCTS AND USES THEREOF

[75] Inventor: Jeffery C. Gee, Kingwood, Tex.

[73] Assignee: Chevron Chemical Company LLC, San Francisco, Calif.

[21] Appl. No.: 09/000,988

[22] Filed: Dec. 30, 1997

[51] Int. Cl.[7] .............................. E21B 21/00; C09K 7/00
[52] U.S. Cl. ..................... 507/267; 507/260; 507/209; 507/116
[58] Field of Search ................................ 507/267, 260, 507/209, 116, 129, 138; 560/247

[56] References Cited

U.S. PATENT DOCUMENTS

| | | | |
|---|---|---|---|
| 3,412,111 | 11/1968 | Irwin et al. | 549/255 |
| 4,440,958 | 4/1984 | Gregory et al. | 560/247 |
| 4,447,642 | 5/1984 | Young | 560/247 |
| 4,448,983 | 5/1984 | Young | 560/241.1 |
| 4,465,852 | 8/1984 | Sato | 560/247 |
| 4,499,319 | 2/1985 | Ballantine et al. | 585/467 |
| 4,505,833 | 3/1985 | Lipowski et al. | 507/105 |
| 4,590,294 | 5/1986 | Ballantine et al. | 560/247 |
| 4,665,213 | 5/1987 | Alper et al. | 560/105 |
| 4,665,220 | 5/1987 | Gregory et al. | 560/247 |
| 4,713,183 | 12/1987 | Patel et al. | 507/128 |
| 4,749,808 | 6/1988 | Ballantine et al. | 560/247 |
| 4,861,884 | 8/1989 | Treybig | 544/336 |
| 5,106,516 | 4/1992 | Mueller et al. | 507/138 |
| 5,232,910 | 8/1993 | Mueller et al. | 507/138 |
| 5,403,822 | 4/1995 | Mueller et al. | 507/138 |
| 5,441,927 | 8/1995 | Mueller et al. | 507/138 |
| 5,593,953 | 1/1997 | Malchow, Jr. | 507/135 |
| 5,593,954 | 1/1997 | Malchow, Jr. | 507/135 |
| 5,617,920 | 4/1997 | Dovan et al. | 166/295 |
| 5,620,946 | 4/1997 | Jahnke et al. | 507/131 |
| 5,637,557 | 6/1997 | Jahnke et al. | 507/246 |
| 5,707,940 | 1/1998 | Bush et al. | 507/138 |

OTHER PUBLICATIONS

A. A. Patwardhan et al., "Esterification of Carboxylic Acids with Olefins Using Cation–Exchange Resins as Catalysts", *Reactive Polymers*, 13 (1990) 161–176, Elsevier Science Publishers B.V., Amsterdam.

*Primary Examiner*—Gabrielle Brouillette
*Assistant Examiner*—LaToya Cross
*Attorney, Agent, or Firm*—W. Bradley Haymond; James W. Ambrosius

[57] ABSTRACT

An esterification process and the products resulting from it which achieves a mixture of secondary esters which are effectively used with invert drilling muds, the process involving the addition of one or more $C_1$–$C_5$ carboxylic acids and one or more $C_3$–$C_{22}$ olefins in the presence of an acid catalyst.

6 Claims, 3 Drawing Sheets

METHOD OF CONVERTING OLEFINS INTO MIXTURES OF SECONDARY ESTERS, PRODUCTS AND USES THEREOF

FIELD OF THE INVENTION

The invention relates to a process for combining an olefin and a carboxylic acid to produce a mixture containing secondary esters; the mixture of esters produced by the process and the use of the mixture of esters.

BACKGROUND OF THE INVENTION

It is known that carboxylic acids can be added to olefins to produce secondary esters (meaning an ester in which the carbon on the alkyl chain to which the carboxylate moiety is attached is a secondary carbon, i.e., one that is covalently bound to two other carbon atoms, rather than a primary or tertiary carbon, which are covalently bound to one or three carbon atoms, respectively). These methods generally involve reaction of a low molecular weight olefin with a high molecular weight carboxylic acid to produce secondary esters.

Catalysts known to be effective in such esterification reactions can be in the form of metallosilicates, especially aluminum silicates (such as zeolites or zeolite mordenites) having exchangeable cations and hydrogen ion-exchanged, layered clays. For esterification reactions, these catalysts are often used with a strong acid added to them.

With hydrogen ion-exchanged, layered clays, it is also known that if the exchangeable cation in the layered clay is a metal cation, there is no need for strong acids to be added to the catalyst. The absence of strong acids renders the clays less corrosive and more readily separable from the reaction mixture.

Stabilized pillared interlayered clay in which the pillars are formed after exchanging the natural cations of the clay with more suitable cations are known to be effective for catalyzing the esterification reaction of olefins and carboxylic acids.

It is also known that monocarboxylic acid methyl esters can be used as the continuous phase or part of the continuous phase in invert drilling muds.

The present invention relates to an esterification reaction of olefins and carboxylic acids which results in a significant decrease in oligomerization and utilizes a catalyst which is relatively easy to prepare and is relatively long-lasting in its effectiveness. The present invention also relates to the product of this esterification reaction which can be used as a component of a drilling fluid.

SUMMARY OF THE INVENTION

An object of the present invention is to provide an invert emulsion drilling fluid comprising:

(a) a continuous phase comprising a mixture of secondary esters selected from the group consisting of propylcarboxylates, butylcarboxylates, pentylcarboxylates, hexylcarboxylates, heptylcarboxylates, octylcarboxylates, nonylcarboxylates, decylcarboxylates, undecylcarboxylates, dodecylcarboxylates, tridecylcarboxylates, tetradecylcarboxylates, pentadecylcarboxylates, hexadecylcarboxylates, heptadecylcarboxylates, octadecylcarboxylates, nonadecylcarboxylates, eicosylcarboxylates, uneicocarboxylates, doeicosylcarboxylates and isomers and mixtures thereof, wherein the secondary esters each have a carboxylate moiety with from one to five carbon atoms;

(b) a weight material; and (c) water.

Still another object of the present invention is to provide a method of making secondary esters comprising combining carboxylic acids having from one to five carbon atoms or isomers or mixtures thereof with olefins selected from the group consisting of propene, butene, pentene, hexene, heptene, octene, nonene, decene, undecene, dodecene, tridecene, tetradecene, pentadecene, hexadecene, heptadecene, octadecene, nonadecene, eicosene, uneicosene, doeicosene and isomers and mixtures thereof in the presence of an acid catalyst.

Yet another object of the present invention is to provide a method of using a mixture of secondary esters as the continuous phase or part of the continuous phase of an invert drilling fluid, the mixture being produced by a method comprising the step of combining carboxylic acids having from one to five carbon atoms or isomers or mixtures thereof with olefins selected from the group consisting of propene, butene, pentene, hexene, heptene, octene, nonene, decene, undecene, dodecene, tridecene, tetradecene, pentadecene, hexadecene, heptadecene, octadecene, nonadecene, eicosene, uneicosene, doeicosene and isomers and mixtures thereof in the presence of an acid catalyst to make secondary esters.

Still another object of the present invention is to provide a method of using a mixture of secondary esters as an additive to water based drilling muds, the mixture being produced by a method comprising the step of combining carboxylic acids having from one to five carbon atoms or isomers or mixtures thereof with olefins selected from the group consisting of propene, butene, pentene, hexene, heptene, octene, nonene, decene, undecene, dodecene, tridecene, tetradecene, pentadecene, hexadecene, heptadecene, octadecene, nonadecene, eicosene, uneicosene, doeicosene and isomers and mixtures thereof in the presence of an acid catalyst to make secondary esters.

DETAILED DESCRIPTION OF THE INVENTION

This invention relates to the use of an acid catalyst, preferably a dry (extremely low moisture) acid washed natural clay, to catalyze the addition of a $C_1$–$C_5$ carboxylic acid to an olefin. The process can utilize one acid or a mixture of acids, and it can utilize one olefin or a mixture of olefins. The process can proceed in batch or continuous mode and operates at 60–300° C. In a continuous mode, the flow rate is generally 0.1–5 WHSV. Some of the most surprising attributes of this invention are (1) that the catalyst must be nearly free of water in order for the esterification reaction to proceed; and (2) that olefin oligomerization is almost eliminated, as long as the concentration of carboxylic acid in the feedstock mixture is kept above about 3 wt. %.

As a hydrophobic synthetic fluid with a pour point below −10° C., a flash point above about 120° C., and a molecular weight near that of a $C_{14}$–$C_{20}$ hydrocarbon, these synthetic mixtures would function well as the continuous phase or part of the continuous phase of an invert mud. Because these mixtures are mixtures of esters rather than hydrocarbons, they would biodegrade more rapidly than do synthetic hydrocarbons.

Another advantage that this invention gives over esters currently used in the drilling industry is that from it can be produced a suitable ester mixture having a lower viscosity than esters currently in use. Currently used esters derive from natural fatty acids, which are typically $C_{12}$ or heavier acids. When combined with a branched $C_8$ or heavier alcohol, which is the conventional practice used to get an ester with a sufficiently low pour point, the resulting ester is more viscous than the ones that can be achieved with the present invention.

The following non-limiting examples show various aspects of various embodiments of the present invention.

EXAMPLES

Example 1
Synthesis of $C_{14}$ Propionates with F-25

F-25® (an acid washed clay)(Engelhard) was dried in a vacuum oven overnight at about 200° C. to remove water. The dried clay granules were packed into a fixed bed, and a mixture that was 50 mole % propionic acid and 50 mole % commercial 1-tetradecene was passed over the bed at a temperature of 140° C. and a flow rate of 0.5 WHSV. By GC/FID analysis, the effluent contained about 20% secondary esters, about 10% propionic acid, about 70% $C_{14}$ olefins, and less than 1% $C_{14}$ oligomers. The single most abundant ester in the mixture was 2-tetradecyl propionate, followed by 3-tetradecyl propionate, followed by 4-tetradecyl propionate, followed by 5-, 6- and 7-tetradecyl propionate. The $C_{14}$ olefins in the effluent were about 70% linear internal olefins and about 30% alpha olefins. The unreacted acid and olefins were separated from the esters by distillation and were suitable for recycling.

Example 2
Synthesis of $C_{14}$ Propionates with F-25

Figure 1:
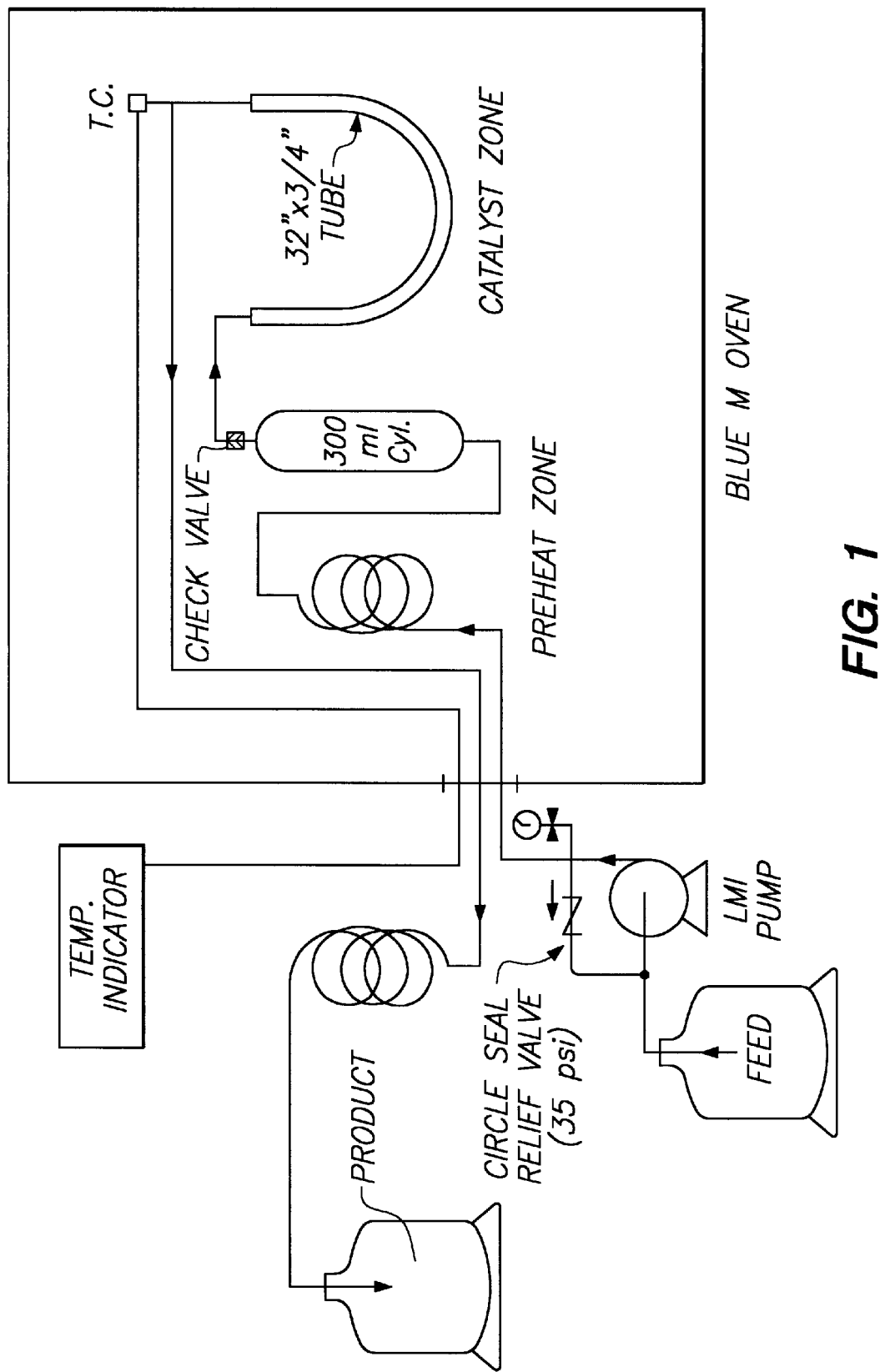
FIG. 1 is a diagram of a continuous unit used to produce mixtures of secondary esters.
Figure 2:
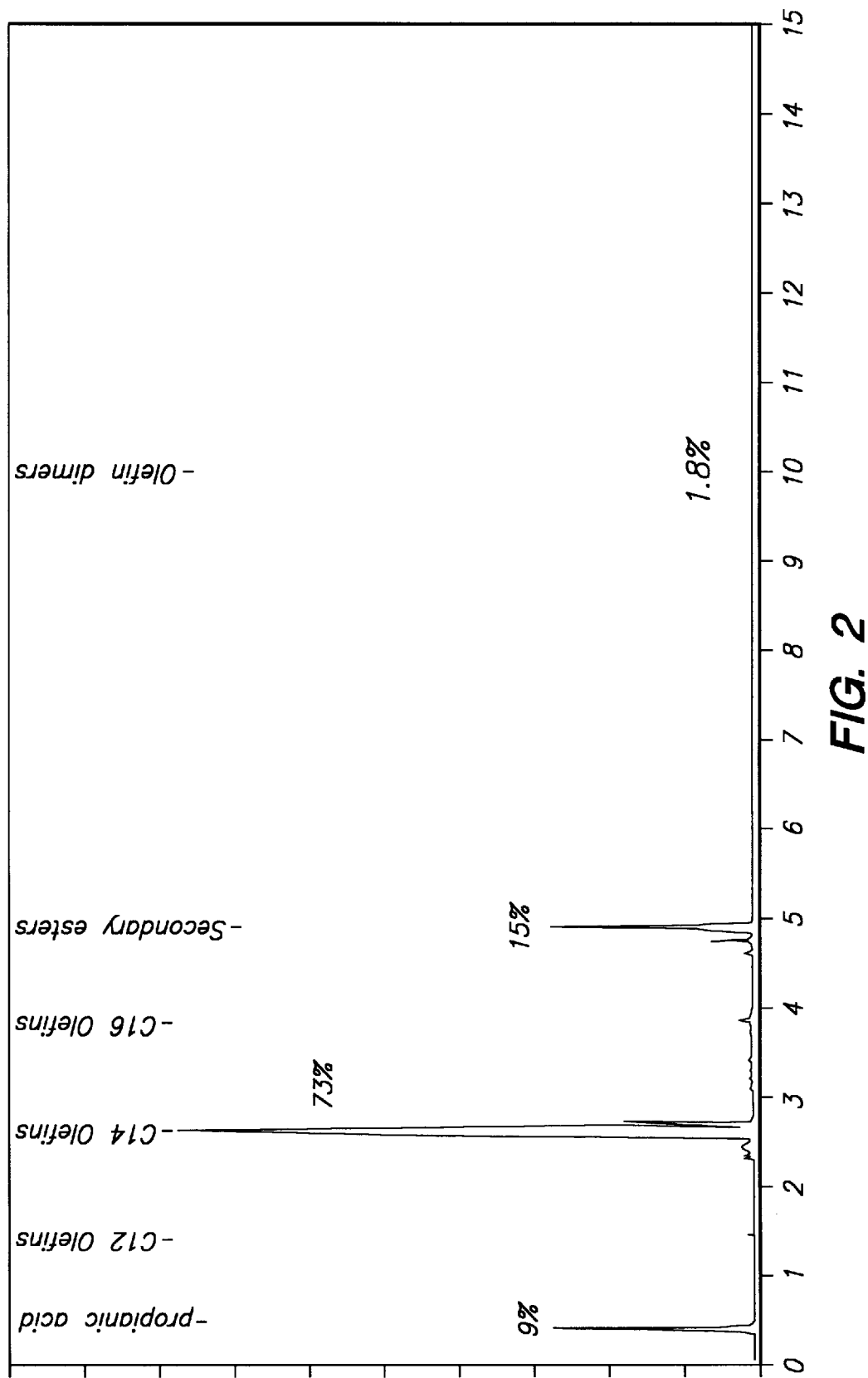
FIG. 2 is a GC/FID chromatogram for a product mixture obtained from the unit when the unit was operating at about 0.65 WHSV and 140° C. as described in Example 2.

F-25® (an acid washed clay)(Engelhard) was dried and packed into a fixed bed as in Example 1. A mixture that was 50 mole % propionic acid and 50 mole % commercial 1-tetradecene was passed over the bed at a temperature of 140° C. and a flow rate of 0.65 WHSV. The chromatogram of FIG. 2 shows the peaks for residual propionic acid and tetradecenes remaining as well as the peaks for the secondary esters formed from tetradecenes and propionic acid formed. By GC/FID analysis, the effluent contained about 9% propionic acid, about 73% tetradecenes, and about 15% secondary esters. Of particular note is the nearly complete absence of peaks for olefin dimers, which, by GC/FID, make up only about 1.8% of the product mixture.

Example 3
Treatment of 1-Dodecene over Filtrol 105

Figure 3:
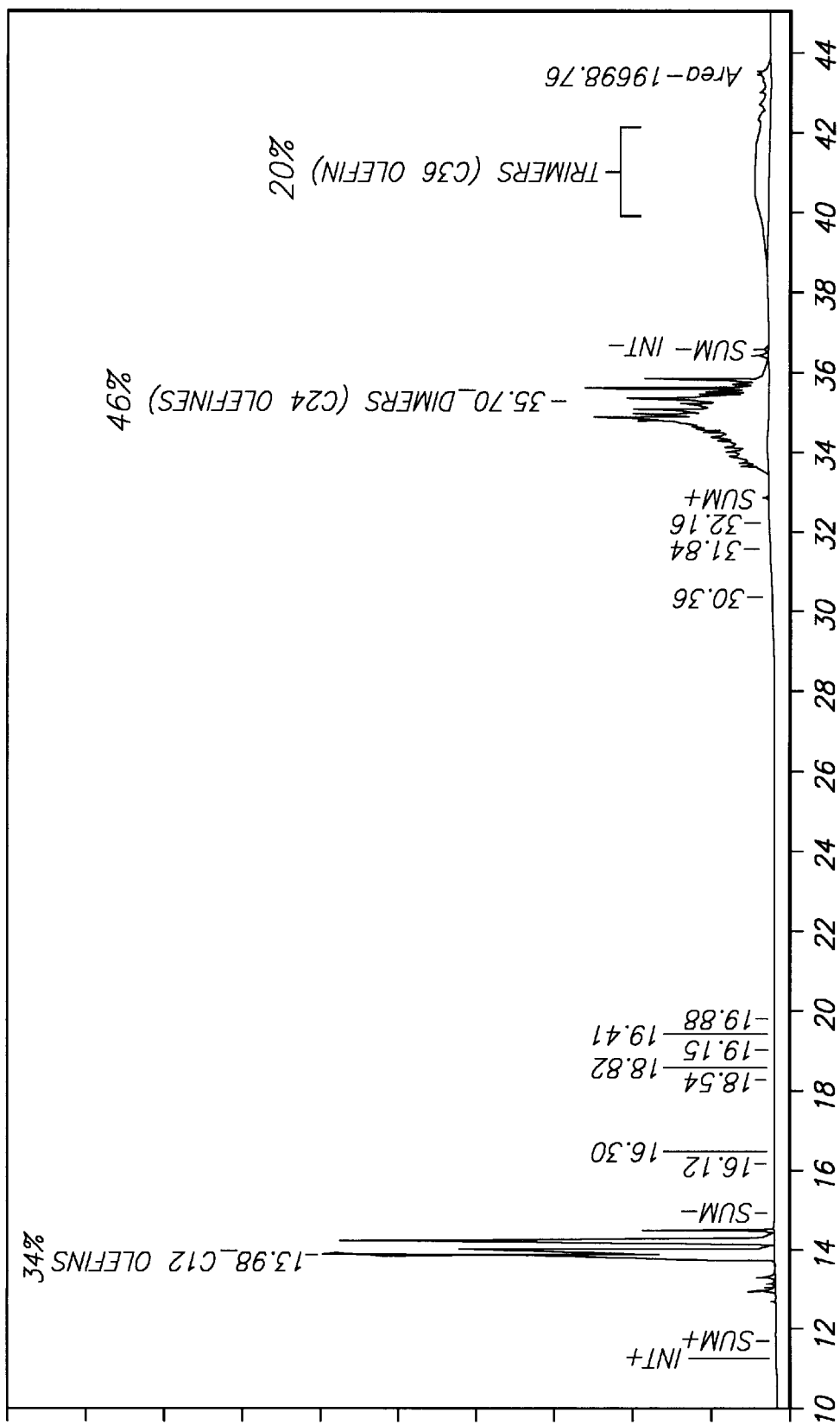
FIG. 3 is a GC/FID chromatogram for a product mixture obtained in a batch reactor when the reactor was operating for about 5 hours at 120° C. as described in Example 3.

As a comparison to the results of Example 2, Filtrol 105® (an acid washed clay)(Engelhard) was dried as in Examples 1 and 2, then added to a batch reactor. A sample of 1-dodecene was stirred and heated over the catalyst at 120° C. for about 5 hours. By GC/FID analysis, the effluent contained about 34% $C_{12}$ olefin monomer, 46% dimer and 20% trimer. In comparing these results with Examples 1 and 2, it can be seen that the presence of propionic acid, especially in an amount greater than about 3% propionic acid in the feed stream, clearly keeps the level of dimer below 5%. The chromatogram of FIG. 3 shows the peaks for the $C_{12}$ oligomers.

Example 4
Stopping Oligomerization Reaction with Propionic Acid

About 598 g of a mixture that was 67 mole % 1-tetradecene and 33 mole % propionic acid was heated and stirred at 140° C. in a batch reactor with 50 g of dry F-25® (an acid washed clay)(Engelhard). After 6.5 hours, the level of secondary esters peaked at about 20% by GC/FID, and olefin oligomers accounted for 3% of the reaction mixture. Instead of remaining steady, the ester level then began to decline, and there was a rapid increase in the amount of olefin oligomer. For the first seven hours of reaction, the propionic acid was >3% (by GC/FID) of the reaction mixture. Once the propionic acid dropped to <3% (by GC/FID) of the reaction mixture, the level of olefin oligomer began to increase rapidly.

Example 5
$C_{14}$ Propionates Evaluated as Base Fluid for Invert Drilling Emulsion The suitability of the $C_{14}$ propionates for use in invert drilling fluids was evaluated. The invert emulsion was prepared by combining most of the components with the base fluid and mixing for 30 minutes at 120° F. using a Gifford Wood homogenizer. The ingredients were added in the order listed in the table below, but the last three were not added during the 30-minute homogenizer cycle. First, the slurry from the homogenizer was transferred to a dispersator, and then the barite, drilling solids, and $CaCl_2$ were added, and the mixture was stirred for 30 minutes. Rheological properties of the resulting drilling fluid were determined at 120° F., before and after hot-rolling the emulsion for 16 hours at 150° F.

| Component | Amount |
| --- | --- |
| $C_{14}$ Propionates | 200.55 ml |
| Water | 37.1 ml |
| Organoclay Viscosifier | 3.0 g |
| Emulsion stabilizer | 8.0 g |
| Emulsifier | 4.0 g |
| Lime | 3.0 g |
| Fluid loss additive | 10.0 g |
| Rheological Modifier | 0.5 g |
| Barite | 334.0 g |
| Simulated drill solids | 20.0 g |
| $CaCl_2$ | 13.1 g |

The drilling fluid showed the following rheological results at 120° F.:

| Parameter | Before hot rolling | After hot rolling |
| --- | --- | --- |
| Fann Dial Reading @ 600 rpm | 81 | 89 |
| Fann Dial Reading @ 300 rpm | 49 | 54 |
| Fann Dial Reading @ 200 rpm | 37 | 41 |
| Fann Dial Reading @ 100 rpm | 25 | 28 |
| Fann Dial Reading @ 6 rpm | 11 | 11 |
| Fann Dial Reading @ 3 rpm | 10 | 10 |
| Plastic Viscosity @ 120° F., cps | 32 | 35 |
| Yield Point, lb/100 sq ft | 17 | 19 |
| 10 s gel strength, lb/100 sq ft | 16 | 16 |
| 10 m gel strength, lb/100 sq ft | 22 | 27 |

-continued

| Parameter | Before hot rolling | After hot rolling |
| --- | --- | --- |
| Electrical stability @ 120° F. | 1328 | 1416 |
| Oil mud alkalinity (Pom) | 1.485 | — |
| Excess lime, lb/bbl | 1.93 | — |
| HTHP filtrate @ 300° F., 500 psi | — | 3.6 |
| Water, ml | — | 0.0 |
| Cake thickness, HTHP, 32$^{nd}$ | — | 2 |

Values of some physical properties of the $C_{14}$ propionates were:

| | |
| --- | --- |
| kinematic viscosity @ 40° C. | 4.25 cSt |
| kinematic viscosity @ 100° C. | 1.56 cSt |
| flash point (° C.) | 156 |
| pour point (° C.) | −29 |
| specific gravity @ 60° F. | 0.86 |

Example 6
Mysid Shrimp Toxicity Test

Additionally, the toxicity to mysid shrimp of the drilling fluid of Example 4 was evaluated according to the US EPA protocol in Appendix 3 of "Effluent Limitation Guidelines and New Source Performance Standards: Drilling Fluids Toxicity Test," Federal Register Vol. 50, No.165, 34631–34636. For cuttings discharge, the drilling fluid must show an $LC_{50}$ toward mysid shrimp of at least 30,000 ppm. The drilling fluid prepared using the $C_{14}$ propionates had an $LC_{50}$ of $\geq 1,000,000$ ppm, indicating the $C_{14}$ propionates make an extremely low toxicity drilling fluid.

Example 7
Synthesis of $C_{12}$ propionates with Dried F-25

A mixture that was 50 mole % propionic acid and 50 mole % commercial 1-dodecene was passed over the same dried F-25® (an acid washed clay)(Engelhard) catalyst as described in Examples 1 and 2. The flow rate was 0.35 WHSV, and the temperature was 140° C. By GC/FID analysis, the effluent contained about 20% secondary esters, about 10% propionic acid, about 70% $C_{12}$ olefins, and less than 1% $C_{12}$ oligomers. The single most abundant ester in the mixture was 2-dodecyl propionate, followed by 3-dodecyl propionate, followed by 4-dodecyl propionate, followed by 5 & 6-dodecyl propionate. The unreacted acid and olefins were separated from the esters by distillation and were suitable for recycle.

Values of some physical properties of the $C_{12}$ propionates were:

| | |
| --- | --- |
| kinematic viscosity @ 40° C. | 3.05 cSt |
| kinematic viscosity @ 100° C. | 1.22 cSt |
| flash point (° C.) | 138 |
| pour point (° C.) | −62 |
| specific gravity @ 60° F. | 0.86 |

Example 8
Synthesis of $C_{12}$ Propionates with Amberlyst 15

A mixture containing 15 g propionic acid, 40 g 1-tetradecene, and 15 g of Amberlyst 15® (a macroreticular, sulfonated, cross-linked copolymer of styrene and divinyl benzene)(Rohm and Haas) was stirred and heated to 140° C. Within 30 minutes, the mixture contained 20% tetradecyl propionates and <1% olefin oligomers by GC/FID. With additional reaction time, the oligomer content increased, and the ester level decreased.

Example 9
Synthesis of $C_{12}$ Propionates with Amberlyst 15

A mixture containing 15 g propionic acid, 40 g 1-tetradecene, and 15 g of Amberlyst 15® (a macroreticular, sulfonated, cross-linked copolymer of styrene and divinyl benzene)(Rohm and Haas) was stirred and heated to 120° C. Within one hour, the mixture contained 31% tetradecyl propionates and <1% olefin oligomers by GC/FID. With additional reaction time, the oligomer content increased, and the ester level decreased.

Example 10
Synthesis of $C_{12}$ Propionates with Amberlyst 15

A mixture containing 15 g propionic acid, 40 g 1-tetradecene, and 15 g of Amberlyst 15® (a macroreticular, sulfonated, cross-linked copolymer of styrene and divinyl benzene)(Rohm and Haas) was stirred and heated to 100° C. Within 1.5 hours, the mixture contained 39% tetradecyl propionates and <1% olefin oligomers by GC/FID. With additional reaction time, the oligomer content increased, and the ester level decreased.

Example 11
Synthesis of $C_{12}$ Propionates with Amberlyst 15

A mixture containing 15 g propionic acid, 40 g 1-tetradecene, and 15 g of Amberlyst 15® (a macroreticular, sulfonated, cross-linked copolymer of styrene and divinyl benzene)(Rohm and Haas) was stirred and heated to 80° C. Within 8 hours, the mixture contained 45% tetradecyl propionates and <1% olefin oligomers by GC/FID. With additional reaction time, the oligomer content increased, and the ester level decreased.

Example 12
Synthesis of $C_{12}$ Propionates with Undried F-25

A mixture containing 8.1 g 1-decene (1 eq), 17.5 g propionic acid (4 eq), and 4.72 g commercial F-25® (an acid washed clay) clay (Engelhard) was stirred and heated to 120° C. (The clay had not been oven dried after purchase.) The mixture refluxed and would not heat above 120° C. After 5 days, the mixture contained 6.5% esters by GC/FID. Then the condenser was removed, and vapor was allowed to leave the reaction vessel. Within 2 hours, the temperature had reached 140° C., and the mixture had reached 11% esters. About 12 hours later, the ester level was 23%.

Example 13
Synthesis of $C_{14}$ Propionates with Dried F-25

A mixture containing 30.0 g 1-tetradecene (1 eq), 34.0 g propionic acid (3 eq), and 10.1 g of F-25® (an acid washed clay) clay (Engelhard) (dried 24 hours in vacuum oven at 200° C.) was stirred and heated to 140° C. The mixture showed no signs of refluxing and easily reached 140° C. Within 20 hours, the mixture contained 35% esters by GC/FID. The ester level remained at this level, even after stirring another 24 hours at the reaction temperature.

Example 14
Synthesis of $C_{14}$ Propionates with Undried F-62

A mixture containing 20.0 g 1-tetradecene (1 eq), 7.58 g propionic acid (1 eq), and 5.0 g F-62® (an acid washed clay) extrudate (Engelhard) was stirred and heated to 120° C. The mixture refluxed and showed only traces of ester by GC/FID, even after 20 hours of heating.

Example 15

Synthesis of $C_{14}$ Propionates with Dried F-62

A mixture containing 40.0 g 1-tetradecene (1 eq), 15.1 g propionic acid (1 eq), and 16.3 g F-62® (an acid washed clay) extrudate (Engelhard) (which had heated in a vacuum oven at 200° C. for 20 hours) was stirred and heated to 140° C. After 19 hours, the mixture contained 31% esters by GC/FID. Additional reaction time did not increase the amount of ester in the mixture.

Example 16

Synthesis of $C_{14}$ Propionates from Isomerized $C_{14}$ and Dried Filtrol 105

A mixture containing 30 g (1 eq) tetradecenes (obtained by thorough double bond isomerization of 1-tetradecene), 34 g (3 eq) propionic acid, and 10 g dry Filtrol 105® (an acid washed clay) clay (Engelhard) (which had heated in a vacuum oven at 200° C. for 20 hours) was stirred and heated to 140° C. After 31 hours, the mixture contained 23% esters by GC/FID. The product esters from this process were the same ones obtained when 1-tetradecene was the starting olefin, but the distribution of propionate isomers was different for this mixture than for those obtained when 1-tetradecene was the starting olefin. There was about as much 7-tetradecyl propionate as 2-tetradecyl propionate in this mixture, showing a much more evenly distributed attachment position for the propionate group in this mixture than for the mixture obtained using 1-tetradecene as the starting olefin.

Example 17

Synthesis of $C_{18}$ Propionates Using Dried F-25

A mixture containing 664 g (1 eq) 1-octadecene, 195 g (1 eq) propionic acid, and 51 g dry F-25® (an acid washed clay)(Engelhard) (which had heated in a vacuum oven at 200° C. for 20 hours) was stirred and heated to 140° C. After 6 hours, the mixture contained 19% secondary esters by GC/FID.

Example 18

$C_{12}$ Propionates Evaluated as Base Fluid for Invert Drilling Emulsion

A mud formulated using a mixture of dodecyl propionates as the base fluid had this composition:

| Component | Amount |
| --- | --- |
| $C_{12}$ Propionates | 200.55 ml |
| Water | 37.1 ml |
| Organoclay Viscosifier | 3.0 g |
| Emulsion stabilizer | 8.0 g |
| Emulsifier | 4.0 g |
| Lime | 3.0 g |
| Fluid loss additive | 10.0 g |
| Rheological Modifier | 0.5 g |
| Barite | 334.0 g |
| Simulated drill solids | 20.0 g |
| $CaCl_2$ | 13.1 g |

The drilling fluid showed the following rheological measurements at 120° F.:

| Parameter | Before hot rolling | After hot rolling |
| --- | --- | --- |
| Mud density, lb/gal | 14.5 | — |
| Fann Dial Reading @ 600 rpm | 74 | 70 |
| Fann Dial Reading @ 300 rpm | 45 | 40 |
| Fann Dial Reading @ 200 rpm | 34 | 30 |
| Fann Dial Reading @ 100 rpm | 21 | 20 |
| Fann Dial Reading @ 6 rpm | 8 | 8 |
| Fann Dial Reading @ 3 rpm | 7 | 7 |
| Plastic Viscosity @ 120° F., cps | 29 | 30 |
| Yield Point, lb/100 sq ft | 16 | 10 |
| 10 s gel strength, lb/100 sq ft | 11 | 10 |
| 10 m gel strength, lb/100 sq ft | 13 | 13 |
| Electrical stability @ 120° F. | 800 | 912 |
| Oil mud alkalinity (Pom) | 1.33 | — |
| Excess lime, lb/bbl | 1.73 | — |
| HTHP filtrate @ 300° F., 500 psi | — | 4.8 |
| Water, ml | — | 0.0 |
| Cake thickness, HTHP, $32^{nd}$ | — | 1 |

Before hot rolling, the mud also showed these properties at 35° F.:

| Parameter | Before hot rolling |
| --- | --- |
| Mud density, lb/gal | 14.5 |
| Fann Dial Reading @ 600 rpm | 238 |
| Fann Dial Reading @ 300 rpm | 130 |
| Fann Dial Reading @ 200 rpm | 92 |
| Fann Dial Reading @ 100 rpm | 50 |
| Fann Dial Reading @ 6 rpm | 10 |
| Fann Dial Reading @ 3 rpm | 8 |
| Plastic Viscosity @ 120° F., cps | 108 |
| Yield Point, lb/100 sq ft | 22 |
| 10 s gel strength, lb/100 sq ft | 14 |
| 10 m gel strength, lb/100 sq ft | 26 |

In the mysid shrimp test, this mud showed an $LC_{50}$ of $\geq 1,000,000$ ppm SPP.

Values of some physical properties of the $C_{12}$ propionates were:

| | |
| --- | --- |
| kinematic viscosity @ 40° C. | 3.05 cSt |
| kinematic viscosity @ 100° C. | 1.22 cSt |
| flash point (° C.) | 138 |
| pour point (° C.) | −62 |
| specific gravity @ 60° F. | 0.86 |

Example 19

$C_{12}/C_{14}$ Propionates Evaluated as Base Fluid for Invert Drilling Emulsion A mud formulated using a mixture of dodecyl propionates (50 wt. %) and tetradecyl propionates (50 wt. %) as the base fluid had this composition:

| Component | Amount |
| --- | --- |
| $C_{12}/C_{14}$ Propionates (1:1) | 200.55 ml |
| Water | 37.1 ml |
| Organoclay Viscosifier | 3.0 g |
| Emulsion stabilizer | 8.0 g |
| Emulsifier | 4.0 g |
| Lime | 3.0 g |
| Fluid loss additive | 10.0 g |

-continued

| Component | Amount |
|---|---|
| Rheological Modifier | 0.5 g |
| Barite | 334.0 g |
| Simulated drill solids | 20.0 g |
| CaCl$_2$ | 13.1 g |

The drilling fluid showed the following rheological measurements at 120° F.:

| Parameter | Before hot rolling | After hot rolling |
|---|---|---|
| Mud density, lb/gal | 14.5 | — |
| Fann Dial Reading @ 600 rpm | 74 | 79 |
| Fann Dial Reading @ 300 rpm | 45 | 46 |
| Fann Dial Reading @ 200 rpm | 34 | 34 |
| Fann Dial Reading @ 100 rpm | 21 | 22 |
| Fann Dial Reading @ 6 rpm | 8 | 8 |
| Fann Dial Reading @ 3 rpm | 7 | 7 |
| Plastic Viscosity @ 120° F., cps | 32 | 33 |
| Yield Point, lb/100 sq ft | 13 | 13 |
| 10 s gel strength, lb/100 sq ft | 12 | 11 |
| 10 m gel strength, lb/100 sq ft | 19 | 15 |
| Electrical stability @ 120° F. | 1086 | 1097 |
| Oil mud alkalinity (Pom) | 1.59 | — |
| Excess lime, lb/bbl | 2.07 | — |
| HTHP filtrate @ 300° F., 500 psi | — | 4.2 |
| Water, ml | — | 0.0 |
| Cake thickness, HTHP, 32$^{nd}$ | — | 1 |

Before hot rolling, the mud also showed these properties at 35° F.:

| Parameter | Before hot rolling |
|---|---|
| Mud density, lb/gal | 14.5 |
| Fann Dial Reading @ 600 rpm | 262 |
| Fann Dial Reading @ 300 rpm | 142 |
| Fann Dial Reading @ 200 rpm | 100 |
| Fann Dial Reading @ 100 rpm | 56 |
| Fann Dial Reading @ 6 rpm | 10 |
| Fann Dial Reading @ 3 rpm | 8 |
| Plastic Viscosity @ 120° F., cps | 120 |
| Yield Point, lb/100 sq ft | 22 |
| 10 s gel strength, lb/100 sq ft | 14 |
| 10 m gel strength, lb/100 sq ft | 26 |

In the mysid shrimp test, this mud showed an LC$_{50}$ of $\geq$1,000,000 ppm SPP.

Example 20

Synthesis of C$_{14}$ Propionates Using H$_2$SO$_4$

A mixture containing 20 g (1 eq) 1-tetradecene, 7.6 g (1 eq) propionic acid, and 0.62 g concentrated sulfuric acid was stirred and heated to 115° C. After 15 hours, the mixture contained 44% secondary esters by GC/FID.

Although a few embodiments of the invention have been described in detail above, it will be appreciated by those skilled in the art that various modifications and alterations can be made to the particular embodiments shown without materially departing from the novel teachings and advantages of the invention. Accordingly, it is to be understood that all such modifications and alterations are included within the spirit and scope of the invention as defined by the following claims.

What is claimed is:

1. A method for preparing an invert drilling fluid comprising the steps of:

(a) preparing a mixture comprising a carboxylic acid having from one to five carbon atoms or isomers or mixtures thereof with olefins selected from the group consisting of propene, butene, pentene, hexene, heptene, octene, nonene, decene, undecene, dodecene, tridecene, tetradecene, pentadecene, hexadecene, heptadecene, octadecene, nonadecene, eicosene, uneicosene, doeicosene and isomers and mixtures thereof, wherein the concentration of the carboxylic acid in the mixture is at least about 3 weight percent;

(b) contacting the mixture of step (a) in the absence of water with an acid catalyst under reaction conditions and for a time sufficient to react said carboxylic acid and said olefins while maintaining the concentration of the carboxylic acid in the reaction mixture above about 3 weight percent to form a mixture of secondary esters; and (c) adding the mixture of secondary esters to an invert drilling mud as the continuous phase or part of the continuous phase of an invert drilling fluid.

2. The method of claim 1 wherein the acid catalyst is an acid washed natural clay.

3. The method of claim 1 wherein the acid catalyst is a macroreticular, sulfonated, cross-linked copolymer of styrene and divinyl benzene.

4. A method for preparing a water based drilling mud comprising the steps of:

(a) preparing a mixture comprising a carboxylic acid having from one to five carbon atoms or isomers or mixtures thereof with olefins selected from the group consisting of propene, butene, pentene, hexene, heptene, octene, nonene, decene, undecene, dodecene, tridecene, tetradecene, pentadecene, hexadecene, heptadecene, octadecene, nonadecene, eicosene, uneicosene, doeicosene and isomers and mixtures thereof, wherein the concentration of the carboxylic acid in the mixture is at least about 3 weight percent;

(b) contacting the mixture of step (a) in the absence of water with an acid catalyst under reaction conditions and for a time sufficient to react said carboxylic acid and said olefins while maintaining the concentration of the carboxylic acid in the reaction mixture above about 3 weight percent to form a mixture of secondary esters; and (c) adding the mixture of secondary esters to a water based drilling mud.

5. The method of claim 4 wherein the acid catalyst is an acid washed natural clay.

6. The method of claim 4 wherein the acid catalyst is a macroreticular, sulfonated, cross-linked copolymer of styrene and divinyl benzene.

* * * * *